United States Patent [19]

Mallams et al.

[11] 4,180,565

[45] Dec. 25, 1979

[54] 1-N-SUBSTITUTED DERIVATIVES OF 4,6-DI-O-(AMINOGLYCOSYL)-1,3-DIAMINOCYCLITOLS

[75] Inventors: Alan K. Mallams, West Orange, N.J.; David H. Davies, Macclesfield, England

[73] Assignee: Schering Corporation, Kenilworth, N.J.

[21] Appl. No.: 909,339

[22] Filed: May 25, 1978

[51] Int. Cl.$^2$ ................... A61K 31/71; C07H 15/22
[52] U.S. Cl. ................... 424/180; 536/10; 536/17 R
[58] Field of Search .............. 536/10, 17; 424/180

[56] References Cited

U.S. PATENT DOCUMENTS

| | | | |
|---|---|---|---|
| 4,053,591 | 10/1977 | Daniels et al. | 536/17 |
| 4,062,947 | 12/1977 | Wright et al. | 536/17 |

*Primary Examiner*—Johnnie R. Brown
*Attorney, Agent, or Firm*—Elizabeth A. Bellamy; Mary S. King

[57] ABSTRACT

Novel 1-N-aminoalkyl (oxycarbonyl or carboxamido or thiocarboxamido) derivatives of 4,6-di-O-(aminoglycosyl)-1,3-diaminocyclitols, useful as antibacterial agents, are described.

17 Claims, No Drawings

4,180,565

1-N-SUBSTITUTED DERIVATIVES OF 4,6-DI-O-(AMINOGLYCOSYL)-1,3-DIAMINOCYCLITOLS

FIELD OF THE INVENTION

This invention relates to novel compositions of matter, to methods for their manufacture, and to methods for their use as antibacterial agents. Specifically, this invention relates to novel 1-N-aminoalkyl (oxycarbonyl or carboxamido or thiocarboxamido) derivatives of 4,6-di-O-(aminoglycosyl)-1,3-diaminocyclitols useful as antibacterial agents. Further, this invention relates to pharmaceutical compositions comprising said 1-N-substituted derivatives, to methods for their manufacture, and to methods for their use in treating bacterial infections.

Particularly, this invention relates to said novel 1-N-substituted derivatives of 4,6-di-O-(aminoglycosyl)-1,3-diaminocyclitol antibiotics, including the gentamicins, kanamycin A, kanamycin B, 3',4'-dideoxykanamycin B, sisomicin, verdamicin, tobramycin, Antibiotics G-52, G-418, 66-40B, 66-40D, JI-20A, JI-20B, the 5-epi-, 5-deoxy-, 5-epi-amino-5-deoxy- analogs of the foregoing, and Antibiotics Mu-1, Mu-4 and Mu-5.

GENERAL DESCRIPTION OF THE INVENTION COMPOSITION-OF-MATTER ASPECT

In its composition-of-matter aspect, this invention relates to certain novel aminoglycosides, and their pharmaceutically acceptable acid addition salts. Particularly, this invention relates to 1-N-X derivatives of 4,6-di-O-(aminoglycosyl)-1,3-diaminocyclitols wherein X is defined by the following formula:

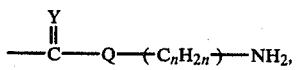

wherein
Y is O, S;
Q is O, NH;
n is 2–6;
with the provisos that:
(a) when Y is S, Q must be NH;
(b) Q and the $NH_2$ functional group cannot be attached to the same carbon atom;
and the pharmaceutically acceptable acid addition salts thereof.

The 4,6-di-O-(aminoglycosyl)-1,3-diaminocyclitols whence our novel 1-N-X derivatives are produced are gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, kanamycin A, kanamycin B, 3',4'-dideoxykanamycin B, sisomicin, verdamicin, tobramycin, Antibiotic G-52, Antibiotic G-418, Antibiotic 66-40B, Antibiotic 66-40D, Antibiotic JI-20A, Antibiotic JI-20B, the 5-epi-, 5-deoxy-, 5-epi-amino-5-deoxy- analogs of the foregoing;
and Antibiotic Mu-1, Antibiotic Mu-4 and Antibiotic Mu-5.

As contemplated in our invention, $C_nH_{2n}$ may be a straight or branched chain alkylene group having from 2 to 6 carbon atoms. Among the straight and branched chain alkylene groups contemplated in our invention are those such as ethylene, n-propylene, isopropylene, n-butylene, isobutylene, tert.-butylene, β-methylpropylene, pentylene, hexylene and the like.

The alkylene group can be attached to Q at any carbon atom in the chain. The $NH_2$ functional group can be attached at any carbon on the chain, except that $NH_2$ and Q may not be attached to the same carbon atom. A further requirement for the compounds of our invention is that when Y is S then Q must be NH.

In those instances where the $NH_2$ group is not on a terminal carbon atom, it may be on a carbon atom which will have, by virtue of this attachment, defined asymmetry. When this is the case, such stereoconfiguration is retained throughout the processes of this invention.

Particularly valuable and preferred compounds of this invention are those wherein Y is O, Q is O or NH, n is 2–3, and the $NH_2$ functional group is on a terminal carbon atom. Such compounds are as follows.

(a) 1-N-(2-aminoethoxycarbonyl)gentamicin B,
(b) 1-N-(2-aminoethoxycarbonyl)sisomicin,
(c) 1-N-(2-aminoethoxycarbonyl)kanamycin A,
(d) 1-N-(2-aminoethoxycarbonyl)gentamicin $C_{1a}$,
(e) 1-N-(2-aminoethoxycarbonyl)-5-epi-sisomicin,
(f) 1-N-(2-aminopropoxycarbonyl)gentamicin B,
(g) 1-N-(2-aminopropoxycarbonyl)kanamycin A,
(h) 1-N-(2-aminopropoxycarbonyl)sisomicin,
(i) 1-N-(2-aminopropoxycarbonyl)gentamicin $C_{1a}$,
(j) 1-N-(2-aminopropoxycarbonyl)-5-epi-sisomicin,
(k) 1-N-(2-aminoethylcarboxamido)gentamicin B,
(l) 1-N-(2-aminoethylcarboxamido)sisomicin.

Also included within the composition-of-matter aspect of this invention are the pharmaceutically acceptable acid addition salts of our 1-N-X derivatives. The salts which we contemplate are made according to known procedures such as by neutralizing the free base with the appropriate acid, usually to about pH 5. Included among the pharmaceutically acceptable acid addition salts of this invention are those derived from organic acids such as succinic, fumaric, and maleic, or preferably from inorganic acids such as hydrochloric, sulfuric, phosphoric, and hydrobromic. The physical embodiments of the acid addition salts of this invention are characterized by being white solids which are soluble in water, sparingly soluble in most polar organic solvents, and insoluble in most non-polar organic solvents.

PROCESS ASPECT OF THE INVENTION

The 4,6-di-O-(aminoglycosyl)-1,3-diaminocyclitol starting compounds of our invention, for example, gentamicins A, B, $B_1$, $C_1$, $C_{1a}$... et al, are known antibiotics. The methods for the preparation of their 5-epi-, 5-deoxy-, and 5-epi-amino-5-deoxy- analogs are described in U.S. Pat. No. 4,000,261, U.S. Pat. No. 4,053,591, and in U.S. Pat. No. 4,000,262, respectively. In general, we have found it preferable to prepare the 5-epi- analogs prior to preparing our 1-N-X derivatives.

The novel pseudotrisaccharides of our invention, that is, the 1-N-X-4,6-di-O-(aminoglycosyl)-1,3-diaminocyclitols wherein X is an aminoalkyloxycarbonyl, an aminoalkylcarboxamido or an aminoalkylthiocarboxamido derivative as defined hereinabove, are prepared by elaboration of techniques as described hereinbelow.

In general, an active ester derivative of a suitably N-protected amino alcohol is reacted with a 1-N-unsubstituted-per- or poly-N-protected aminoglycoside and the resulting 1-N-substituted per- or poly-N-protected aminoglycoside is then deprotected. For example, N-(2- benzyloxycarbonylaminoethoxycarbonyloxy)succinimide is reacted with 3,6'-di-N-benzyloxycarbonyl-gentamicin B in the presence of triethylamine to produce 3,6'-di-N-benzyloxycarbonyl-1-N-(2-benzyloxycarbonylaminoethoxycarbonyl)gentamicin B, which compound is then deprotected to produce 1-N-(2-aminoethoxycarbonyl)-gentamicin B.

By suitably protected, we mean those groups utilized to protect amino groups during chemical reactions but which are easily removed after a desired transformation has taken place. Our preferred amino protecting groups are benzyloxycarbonyl, 2,2,2-trichloroethoxycarbonyl, 4-methoxybenzyloxycarbonyl, trifluoroacetyl, which hereinafter may be referred to as CBZ, TCEC, PMZ and TFA. The choice of the protecting group depends on various factors including which amino group is being protected, subsequent reaction conditions and the compatibility of both the substrate and 1-N-substituent to the conditions required for the removal of the protecting groups. The preparations and examples described hereinbelow are illustrative of many of the protecting groups which can be used to obtain the compounds of our invention. Generally speaking, however, we have found that PMZ is our preferred amino protecting group.

Within the confines of this invention, we define "poly" protected to mean an aminoglycoside wherein specific amino groups that are unprotected are enumerated and any remaining amino groups may or may not be protected. A per-N-protected compound is that compound in which an unprotected amino group is specifically enumerated and any other remaining amino groups must be protected.

As exemplified hereinbelow, the 1-N-aminoalkyloxycarbonyl

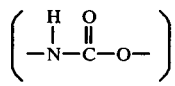

derivatives may be prepared from per- or poly-N-protected aminoglycosides. The only requirements for the protecting groups in this instance are that they should be readily removable without hydrolyzing the oxycarbonyl side chain. In those substrates wherein there exists 4',5'-unsaturation, such as sisomicin, verdamicin, the choice of protecting groups must be such that removal techniques will not interfere with the 4',5'-unsaturation. For instance, it is then preferable to use TCEC, PMZ or TFA rather than CBZ since the latter group requires hydrogenation techniques for removal which would also hydrogenate the 4',5'-double bond.

When 1-N-aminoalkylcarboxamido and 1-N-aminoalkylthiocarboxamido derivatives are prepared, we have found that the starting aminoglycoside must preferably have per-N-protection, i.e., have all the amino groups with the exception of the 1-amino group protected. The reactivity of the isocyanate/isothiocyanate intermediates necessitates this per-N-protection, as these intermediates demonstrate less selectivity for the 1-amino group when other amino groups in the substrate are unprotected. For example, 1-N-unsubstituted-3,6',3''-tri-N-CBZ-gentamicin B is reacted with 2-azidoethylisocyanate to obtain 3,6',3''-tri-N-CBZ-1-N-azidoethylcarboxamido-gentamicin B which, in turn, is converted to 1-N-2-aminoethylcarboxamido-gentamicin B. It is necessary, when converting the 1-N-azidoethylcarboxamido/azidoethylthiocarboxamido derivatives to the corresponding amines, to avoid vigorous hydrogenation (or reductive) techniques in those aminoglycosides wherein there is 4',5'-unsaturation. We have found particularly useful a special hydrogenation technique, i.e., Lindlar's catalyst, which will selectively reduce azides to amines in the presence of other groups that would normally undergo hydrogenation.

We usually use N-hydroxysuccinimide to prepare the active ester derivatives of the N-protected-amino alcohols but other active esters can be utilized such as those derived from N-hydroxyphthalimide.

METHOD-OF-USE AND PHARMACEUTICAL COMPOSITION ASPECT

The present invention includes within its scope the method of eliciting an antibacterial response in a warm blooded animal having a susceptible bacterial infection which comprises administering to said animal a non-toxic, antibacterially effective amount of a 1-N-aminoalkyl (oxycarbonyl or carboxamido or thiocarboxamido)-4,6-di-O-(aminoglycosyl)-1,3-diaminocyclitol of this invention. Also included within our inventive concept are pharmaceutical compositions comprising a non-toxic, antibacterially effective amount of a compound of this invention together with a non-toxic, pharmaceutically acceptable carrier.

In general, the compounds of our invention and their pharmaceutically acceptable acid addition salts exhibit activity against a broad range of gram-negative pathogens and have a spectrum similar to and a potency similar to or greater than amikacin and 1-N-HAPA-gentamicin B. The pathogenic types of bacteria against which our compounds exhibit activity are the gram-negatives such as $E.$ $coli,$ Klebsiella, Proteus, Providencia, Pseudomonas, Salmonella, and Serratia, and the gram-positives such as Staphylococcus and $B.$ $subtilis.$ The derivatives of sisomicin, 5-epi-sisomicin, and gentamicin $C_{1a}$ (especially the 1-N-(2-aminoethoxycarbonyl) derivatives) are our most preferred compounds. These compounds when compared to amikacin and 1-N-HAPA-gentamicin B advantageously exhibit the following comparative activities:

(a) they are active against 2'-acetylating strains,
(b) they are more active against various 3- and 6'-acetylating strains
(c) they are more active against 2''-adenylylating strains, which are common in gram-negative bacteria,
(d) they are highly active against 3'-phosphorylating strains and 4'-adenylylating strains which have been found in Staphylococcus; these two strains are not susceptible to amikacin or 1-N-HAPA-gentamicin B.

The compounds of our invention can be used alone or in combination with other antibiotic agents to prevent the growth or reduce the number of bacteria in various environments. Their activity against gram-negative bacteria renders them useful in combatting infection in human or veterinary applications. Additionally, our compounds may also be used to disinfect laboratory glassware, dental and medical equipment.

In general, the dosage administered of our compounds will be dependent on the age and weight of the animal species being treated, mode of administration and the type and severity of bacterial infection being prevented or reduced.

The compounds of our invention may be administered orally, compounded in the form of tablets, capsules, elixirs or the like, or administered with animal feed. It is in these dosage forms that these antibacterials are most effective for treating bacterial infections of the gastrointestinal tract, which infections cause diarrhea. They are also useful in pre- and post-operative gut sterilization.

In liquid form they may be administered parenterally via intramuscular, intravenous, subcutaneous and intrasternal injection. The injectable solution or suspension will usually be administered at from about 1 mg. to about 30 mgs. of antibacterial per kilogram of body weight per day divided into about 2 to about 4 doses. The precise dose will depend on the stage and severity of the infection, the susceptibility of the infecting organism to the antibacterial and the individual characteristics of the animal species being treated. They may also be utilized in liquid form such as solutions, suspensions and the like, for otic and ophthalmic use.

Further, the compounds of this invention may be applied topically in the form of ointments, both hydrophilic and hydrophobic, lotions which may be aqueous, non-aqueous or other emulsion types, or in creams or gels. In general, the topical applications will contain from about 0.1 to about 3.0 gms. of the active per 100 gms. of ointment, cream or lotion. The topical preparations are usually gently applied to lesions from about 2 to about 5 times a day.

The pharmaceutical carriers useful in the preparation of all the foregoing formulations will include, for example, such substances as water, oils, fats, waxes, polyesters, alcohols, polyols and the like.

The invention described hereinabove is illustrated in detail hereinbelow in the Preparations, Examples and Formulations, which is not to be construed as limiting the scope of our invention.

PREPARATIONS

Preparation I

N-Protected Amino Alcohols

A. 2-Benzyloxycarbonylaminoethanol

2-Aminoethanol (20 g.) and sodium carbonate (84.8 g.) is dissolved in acetone-water (1:1) (500 ml.) and benzylchloroformate (83.9 g.) is added dropwise to the stirred solution at 0° C. over a period of 0.5 hours. The mixture is stirred at 0° C. for a further 2.5 hours. The solids are filtered off and washed with acetone and the filtrate is evaporated to dryness. The resulting gum is taken up in chloroform and filtered. The filtrate is evaporated to dryness. The residue is chromatographed on a silica gel column (140×5 cm.) using chloroform and then 10% methanol in chloroform as the eluant to give 2-benzyloxycarbonylaminoethanol, which crystallizes from hexane as colorless needles; m.p. 53°–55° C.; $\gamma$ max (CCl$_4$) 3450, 3325, 1720, 1510, 1245 cm$^{-1}$; $\delta$ (CDCl$_3$) 3.29 (2H, m HOCH$_2$C$\underline{H_2}$NH—), 3.57 (2H, m, HOC$\underline{H_2}$CH$_2$NH—), 5.07 (2H, s, —C$\underline{H_2}$C$_6$H$_5$) and 7.31 ppm (5H, s, —CH$_2$C$_6$$\underline{H_5}$).

B. 3-Benzyloxycarbonylaminopropanol

In a manner similar to Preparation IA, by substituting 3-aminopropanol for 2-aminoethanol, there is obtained 3-benzyloxycarbonylaminopropanol; m.p. 47°–49° C.; m/e 209 (M.+); $\nu$ max (KBr) 3320, 1680, 1535 cm$^{-1}$; $\delta$ (CDCl$_3$) 1.67 (2H, m, J=7.5 Hz, 2—CH$_2$), 3.28 (2H, dt, J=7.5 Hz, 3—CH$_2$), 3.62 (2H, t, J=7.5 Hz, 1—CH$_2$), 5.08 (2H, s, —C$\underline{H_2}$C$_6$H$_5$) and 7.34 ppm (5H, s, —CH$_2$C$_6$$\underline{H_5}$).

C. 4-Benzyloxycarbonylamino-1-Butanol

In a manner similar to Preparation IA, by substituting 4-amino-1-butanol for 2-aminoethanol, there is obtained 4-benzyloxycarbonylamino-1-butanol as a colorless amorphous solid; m.p. 80°–81° C.; m/e 223 (M.+); $\nu$ max (KBr) 3325, 1690, 1545, 1060 cm$^{-1}$; $\delta$ (CDCl$_3$) 1.56 (4H, m, CbzNHCH$_2$(C$\underline{H_2}$)$_2$CH$_2$OH), 1.73 (1H, broad s, —OH), 3.18 (2H, m, CbzNHC$\underline{H_2}$(CH$_2$)$_2$CH$_2$OH), 3.60 (2H, m, CbzNHCH$_2$(CH$_2$)$_2$C$\underline{H_2}$OH), 5.09 (2H, s, C$_6$H$_5$C$\underline{H_2}$—) and 7.38 ppm (5H, s, C$_6$$\underline{H_5}$CH$_2$—).

D. (2R)-2-Benzyloxycarbonylamino-1-Butanol

In a manner similar to Preparation IA, by substituting (2R)-2-amino-1-butanol for 2-aminoethanol, there is obtained (2R)-2-benzyloxycarbonylamino-1-butanol as a waxy solid; m/e 192 (M.+—31); $[\alpha]_D^{26}$ +19.0° (CHCl$_3$); $\nu$ max (KBr) 3400, 3250, 1700, 1540 cm$^{-1}$; $\delta$ (CDCl$_3$), 0.90 (3H, t, J 8 Hz, 4—CH$_3$), 1.48 (2H, m, 3—CH$_2$), 3.05 (1H, m, 2—CH), 3.55 (2H, m, 1—CH$_2$), 5.08 (2H, s, —C$\underline{H_2}$C$_6$H$_5$) and 7.34 ppm (5H, s, —CH$_2$C$_6$$\underline{H_5}$).

E. (2S)-2-Benzyloxycarbonylamino-4-Methyl-1-Pentanol

In a manner similar to Preparation IA, by substituting (2S)-2-amino-4-methyl-1-pentanol (L-leucinol) for 2-aminoethanol, there is obtained (2S)-2-benzyloxycarbonylamino-4-methyl-1-pentanol as a waxy solid; m/e 251 (M.+); $[\alpha]_D^{26}$ −27.6° (CHCl$_3$); $\nu$ max (KBr) 3400, 3325, 1695, 1530 cm$^{-1}$; $\delta$ (CDCl$_3$), 0.91 (6H, d, J 8 Hz, —(C$\underline{H_3}$)$_2$), 5.08 (2H, s, —C$\underline{H_2}$C$_6$H$_5$) and 7.34 ppm (5H, s, —CH$_2$C$_6$$\underline{H_5}$).

F. 2-(2,2,2-Trichloroethoxycarbonylamino)Ethanol

2-Aminoethanol (20 g.) and sodium carbonate (27.8 g.) is dissolved in acetone-water (4:1) (500 ml.) and 2,2,2-trichloroethylchloroformate (104.2 g.) is added dropwise to the stirred solution at 0° C. over a period of 0.5 hours. The mixture is stirred at 0° C. for a further 3 hours. The solids are filtered off and washed with acetone and the filtrate is evaporated to dryness. The resulting gum is taken up in chloroform (500 ml.) and washed with water (3×100 ml.). The chloroform solution is evaporated to dryness to give 2-(2,2,2-trichloroethoxycarbonylamino)ethanol; $\nu$ max (film), 3300, 2910, 1700, 1520, 1240, 1140, 1055, cm$^{-1}$; $\delta$ (CDCl$_3$) 3.43 (2H, t, J 7.5 Hz, HOCH$_2$C$\underline{H_2}$NH—), 3.77 (2H, t, J 7.5 Hz, HOC$\underline{H_2}$CH$_2$NH—) and 4.77 ppm (2H, s, —COOC$\underline{H_2}$CCl$_3$).

G. 2-(4-Methoxybenzyloxycarbonylamino)-Ethanol

2-Aminoethanol (1.5 g.) is dissolved in water (200 ml.) containing triethylamine (4.83 g.) and 4-methoxybenzyl-S-(4,6-dimethylpyrimidin-2-yl)-thiolcarbonate (10.67 g.) in dioxane (200 ml.) is added to the stirred solution. Stirring is continued for 2 hours at 25° C. and the mixture is evaporated to dryness. The residue is dissolved in chloroform and extracted with 0.1 N hydrochloric acid (3×25 ml.). The chloroform is washed with water, dried (MgSO$_4$) and evaporated to obtain 2-(4-methoxybenzyloxycarbonylamino)-ethanol; $\nu$ max (nujol) 3250, 1680, 1535, 1240, 1050 cm$^{-1}$; $\delta$ (CDCl$_3$) 2.40 (1H, s, —OH), 3.38 (2H, m, —NHC$\underline{H_2}$CH$_2$O—); 3.71 (2H, t, J=5 Hz, —NHCH$_2$C$\underline{H_2}$—O—); 3.82 (3H, s, CH$_3$O—); 5.06 (2H, s, CH$_3$OC$_6$H$_4$C$\underline{H_2}$OCO—); 6.90 (2H, d, J=9 Hz, CH$_3$OC$_6$$\underline{H_4}$CH$_2$OCO—) and 7.35 ppm (2H, d, J=9 Hz, CH$_3$OC$_6$$\underline{H_4}$CH$_2$OCO—).

PREPARATION II

ACTIVE ESTER DERIVATIVES OF N-PROTECTED AMINO ALCOHOLS

A. N-(2-Benzyloxycarbonylaminoethoxycarbonyloxy)succinimide

2-Benzyloxycarbonylaminoethanol (10 g.) is dissolved in methylene chloride (200 ml.) containing phosgene (15.2 g.) and triethylamine (5 ml.) and the mixture is stirred at 25° C. for 3 hours. The solution is evaporated to dryness and the resulting gum is taken up in ethyl acetate and filtered. The filtrate (200 ml.) is added in portions to a solution of N-hydroxy-succinimide (5.9 g.) in ethyl acetate (100 ml.) containing pyridine (10 ml.) and the mixture is stirred at 25° C. for 1 hour. The solution is filtered and the filtrate evaporated to dryness and azeotroped with toluene. The gum is chromatographed rapidly on a silica gel column (110×5 cm.) using 10% increasing to 15% ethyl acetate in methylene chloride as the eluant to give N-(2-benzyloxycarbonylaminoethoxycarbonyloxy)succinimide as a colorless gum; $\nu$ max (CHCl$_3$), 3430, 3005, 1750, 1510, 1220 cm$^{-1}$; $\delta$ (CDCl$_3$), 2.75 (4H, s, —COC$\underline{H}_2$C$\underline{H}_2$CO—), 3.50 (2H, m, —OCH$_2$C$\underline{H}_2$NH), 4.38 (2H, m, —OC$\underline{H}_2$CH$_2$NH—), 5.12 (2H, s, —C$\underline{H}_2$C$_6$H$_5$), and 7.35 ppm (5H, s, —CH$_2$C$_6\underline{H}_5$).

B. N-(3-Benzyloxycarbonylaminopropoxycarbonyloxy)succinimide

In a manner similar to Preparation IIA, by substituting 3-benzyloxycarbonylaminopropanol for 2-benzyloxycarbonylaminoethanol, there is obtained N-(3-benzyloxycarbonylaminopropoxycarbonyloxy)succinimide; m/e 350 (M.+); $\nu$ max (film) 3300, 1780, 1750, 1740, 1710, 1520, 1210 cm$^{-1}$; $\delta$ (CDCl$_3$), 1.92 (2H, m, J=7.5 Hz, 2—CH$_2$), 2.73 (4H, s, —COC$\underline{H}_2$C$\underline{H}_2$CO—), 3.30 (2H, dt, J=7.5 Hz, 3—CH$_2$), 4.35 (2H, t, J=7.5 Hz, 1—CH$_2$), 5.10 (2H, s, —C$\underline{H}_2$C$_6$H$_5$) and 7.36 ppm (5H, s, —CH$_2$C$_6\underline{H}_5$).

C. N-(4-Benzyloxycarbonylaminobutoxycarbonyloxy)succinimide

In a manner similar to Preparation IIA, by substituting 4-benzyloxycarbonylamino-1-butanol for 2-benzyloxycarbonylaminoethanol, there is obtained N-(4-benzyloxycarbonylaminobutoxycarbonyloxy)succinimide as a colorless gum; m/e 364 (M.+); $\nu$ max (film), 3350, 1830, 1780, 1720, 1530, 1220 cm$^{-1}$; $\delta$ (CDCl$_3$), 1.68 (4H, m, CbzNHCH$_2$(C$\underline{H}_2$)$_2$CH$_2$O—), 2.74 (4H, s, —COC$\underline{H}_2$C$\underline{H}_2$CO—), 3.23 (2H, m, CbzNHC$\underline{H}_2$—), 4.36 (2H, t, J 7.5 Hz, —C$\underline{H}_2$O—), 5.07 (2H, s, C$_6$H$_5$C$\underline{H}_2$—) and 7.40 ppm (5H, s, C$_6\underline{H}_5$CH$_2$—).

D. (2R)-N-(2-Benzyloxycarbonylaminobutoxycarbonyloxy)succinimide

In a manner similar to Preparation IIA, by substituting (2R)-2-benzyloxycarbonylamino-1-butanol for 2-benzyloxycarbonylaminoethanol, there is obtained (2R)-N-(2-benzyloxycarbonylaminobutoxycarbonyloxy)succinimide as a yellow gum; m/e 364 (M.+); $[\alpha]_D^{26}$ +20.8° (CHCl$_3$); $\nu$ max (liquid film) 3300, 1830, 1780, 1720, 1530, 1220 cm$^{-1}$; $\delta$ (CDCl$_3$) 0.95 (3H, t, J 6 Hz, C$\underline{H}_3$CH$_2$—), 1.51 (2H, dq, J 6 Hz, CH$_3$C$\underline{H}_2$—), 2.58 (1H, broad s, NH—), 2.79 (4H, s, —COC$\underline{H}_2$C$\underline{H}_2$CO—), 3.69 (1H, m, >CHNHCbz), 4.35 (2H, d, J 4 Hz, —CH$_2$O—), 5.13 (2H, s, C$_6$H$_5$C$\underline{H}_2$—) and 7.20 ppm (5H, s, C$_6\underline{H}_5$CH$_2$—).

E. (2S)-N-(2-Benzyloxycarbonylamino-4-Methylpentoxycarbonyloxy)Succinimide

In a manner similar to Preparation IIA, by substituting (2S)-2-benzyloxycarbonylamino-4-methyl-1-pentanol for 2-benzyloxycarbonylaminoethanol, there is obtained (2S)-N-(2-benzyloxycarbonylamino-4-methylpentoxycarbonyloxy)succinimide as a colorless gum; m/e 392 (M.+); $[\alpha]_D^{26}$ −28.3° (CHCl$_3$); $\nu$ max (liquid film) 3300, 1810, 1780, 1720, 1520, 1210 cm$^{-1}$; $\delta$ (CDCl$_3$) 0.93 (3H, d, J 6 Hz, (C$\underline{H}_3$)$_2$CH—), 0.95 (3H, d, J 6 Hz, (C$\underline{H}_3$)$_2$CH—), 1.20-1.70 (3H, m, (CH$_3$)$_2$C$\underline{H}$CH$_2$—), 2.58 (1H, broad s, N$\underline{H}$), 2.75 (4H, s, —COC$\underline{H}_2$C$\underline{H}_2$CO—), 4.03 (1H, m, >C$\underline{H}$NHCbz), 4.30 (2H, m, —OC$\underline{H}_2$—), 5.10 (2H, s, C$_6$H$_5$C$\underline{H}_2$O—) and 7.37 ppm (5H, s, C$_6\underline{H}_5$CH$_2$—).

F. N-[2-(2,2,2-Trichloroethoxycarbonylamino)ethoxycarbonyloxy]Succinimide

In a manner similar to Preparation IIA, by substituting 2-(2,2,2-trichloroethoxycarbonylamino)ethanol for 2-benzyloxycarbonylaminoethanol, there is obtained N-[2-(2,2,2-trichloroethoxycarbonylamino)ethoxycarbonyloxy]succinimide, which is purified by preparative thin layer chromatography on silica gel plates using 20% ethyl acetate in methylene chloride as the eluant: $\nu$ max (film), 3330, 2950, 1820, 1790, 1740, 1725, 1530, 1220 cm$^{-1}$; $\delta$ (CDCl$_3$) 2.83 (4H, s, —COC$\underline{H}_2$CH$_2$CO—), 3.60 (2H, m, —OCH$_2$C$\underline{H}_2$NH—), 4.47 (2H, t, J 7.5 Hz, —OC$\underline{H}_2$CH$_2$NH—) and 4.78 ppm (2H, s, —COOC$\underline{H}_2$CCl$_3$).

G. N-[2-(4-Methoxybenzyloxycarbonylamino)-Ethoxycarbonyloxy]Succinimide

In a manner similar to Preparation IIA, by substituting 2-(4-methoxybenzyloxycarbonylamino)ethanol for 2-benzyloxycarbonylaminoethanol, there is obtained N-[2-(4-methoxybenzyloxycarbonylamino)ethoxycarbonyloxy]succinimide: $\nu$ max (film), 3300, 1800, 1780, 1730, 1700, 1500, 1230, 1210 cm$^{-1}$; $\delta$ (CDCl$_3$) 2.76 (4H, s, —COC$\underline{H}_2$C$\underline{H}_2$CO—), 3.47 (2H, m, —NHC$\underline{H}_2$CH$_2$O—), 3.78 (3H, s, CH$_3$O—), 4.36 (2H, t, J=5 Hz, —NHCH$_2$C$\underline{H}_2$O—), 5.02 (2H, s, CH$_3$OC$_6$H$_4$C$\underline{H}_2$OCO—), 5.48 (1H, m, —NH—), 6.82 (2H, d, J=9 Hz, CH$_3$OC$_6\underline{H}_4$CH$_2$OCO—), and 7.27 ppm (2H, d, J=9 Hz, CH$_3$OC$_6\underline{H}_4$CH$_2$OCO—).

PREPARATION III

Poly and Per-N-Protected-4,6-Di-Q-(Aminoglycosyl)-1,3-Diaminocyclitols

A. 3,6'-Di-N-Benzyloxycarbonyl-1-N-(2,2,2-Trichloroethoxycarbonyl)Gentamicin B 3,6'-Di-N-benzyloxycarbonylgentamicin B (10.73 g.) is dissolved in dry dimethylformamide (800 ml.). N-(2,2,2-Trichloroethoxycarbonyloxy)succinimide (3.6 g.) is added and the mixture is stirred at 25° C. for 2 hours with exclusion of moisture. The mixture is evaporated to dryness and the gum is chromatographed on a silica gel column (120×5 cm.) using the lower phase of a chloroform-methanol-concentrated ammonium hydroxide solution (2:1:1) as the eluant to give 3,6'-di-N-benzyloxycarbonyl-1-N-(2,2,2-trichloroethoxycarbonyl)-gentamicin B as a colorless amorphous solid; $[\alpha]_D^{26}$ +70.8° (CH$_3$OH); $\nu$ max (KBr) 3375, 1705, 1520, 1040 cm$^{-1}$; $\delta$ (CDCl$_3$) 0.94 (3H, s, 4''—CH$_3$), 2.35 (3H, s, 3''—NCH$_3$), 4.88 (6H, s, —C$\underline{H}_2$C$_6$H$_5$ and —C$\underline{H}_2$CCl$_3$) and 7.15 ppm. (10H, s, —CH$_2$C$_6\underline{H}_5$).

B. 3,6',3''-Tri-N-Benzyloxycarbonyl-1-N-(2,2,2-Trichloroethoxycarbonyl)gentamicin B 3,6'-Di-N-benzyloxycarbonyl-1-N-(2,2,2-trichloroethoxycarbonyl)gentamicin B (8.0 g.) and sodium carbonate (4.55 g.) is dissolved in acetone-water (1:1) (400 ml.). Benzylchloroformate (4.4 g.) is added dropwise to the stirred solution at 0° C. over 0.5 hours. The mixture is stirred at 25° C. for 18 hours and then concentrated and extracted with chloroform. The chloroform extracts are washed with water and evaporated to dryness. The resulting solid is chromatographed on a silica gel column (30×2 cm.) using 7% methanol in chloroform as the eluant to give 3,6′,3″-tri-N-benzyloxycarbonyl-1-N-(2,2,2-trichloroethoxycarbonyl)gentamicin B as a colorless solid; $[\alpha]_D^{26}$ +74.7° (CH$_3$OH); $\nu$ max (KBr) 3410, 1700, 1520, 1050 cm$^{-1}$; $\delta$ (CDCl$_3$) 1.00 (3H, broad s, 4″—CH$_3$), 3.00 (3H, broad s, 3″—NCH$_3$), 5.03 (8H, broad s, —C$\underline{H_2}$C$_6$H$_5$ and —C$\underline{H_2}$CCl$_3$) and 7.29 ppm. (15H, broad s, —CH$_2$C$_6$$\underline{H_5}$).

C. 3,6′,3″-Tri-N-Benzyloxycarbonylgentamicin B 3,6′,3″-Tri-N-benzyloxycarbonyl-1-N-(2,2,2-trichloroethoxycarbonyl)gentamicin B (8.0 g.) is dissolved in acetic acid-water (9:1) (500 ml.) and activated zinc (10.41 g.) is added. The mixture is stirred at 25° C. for 7 hours, whereupon additional activated zinc (10.41 g.) is added. The mixture is stirred at 25° C. for a further 16 hours. Additional activated zinc (20.82 g.) is added and the reaction is continued for a further 25 hours. The mixture is concentrated and, after addition of methanol, it is filtered. The solids are washed with methanol and the combined filtrates are evaporated and the residue chromatographed on a silica gel column (160×5 cm.) using the lower phase of a chloroform-methanol-7% ammonium hydroxide solution (2:1:1) as the eluant to give 3,6′,3″-tri-N-benzyloxycarbonylgentamicin B as a colorless amorphous solid; $[\alpha]_D^{26}$ +83.3° (CH$_3$OH); $\nu$ max (KBr) 3400, 1700, 1520, 1050 cm$^{-1}$; $\delta$ (CDCl$_3$), 1.03 (3H, broad s, 4″—CH$_3$), 3.02 (3H, broad s, 3″—NCH$_3$), 5.05 (6H, broad s, —C$\underline{H_2}$C$_6$H$_5$) and 7.25 ppm. (15H, broad s, —CH$_2$C$_6$$\underline{H_5}$).

D. 3,6′-Di-N-(2,2,2-Trichloroethoxycarbonyl)Kanamycin A

Kanamycin A (2 g.) is dissolved in dimethylsulfoxide (100 ml.) containing nickel acetate (5.12 g.) and the mixture is stirred at 25° C. for 0.5 hour. N-[2-(2,2,2-Trichloroethoxycarbonylamino)ethoxycarbonyl]succinimide (2.4 g.) in dimethylsulfoxide (20 ml.) is added dropwise to the stirred solution over a period of 0.5 hour. Additional reagent (240 mg. after 1 hour, 240 mg. after 2 hours, 480 mg. after 3 hours) is added and, after 5 hours, the mixture is poured into diethyl ether (600 ml.) and allowed to stand for 15 minutes. The ether layer is decanted and the residue is washed with 3×600 ml. of diethyl ether. The latter is dissolved in methanol (10 ml.) and hydrogen sulfide is poured through the solution for 0.5 hour. The mixture is filtered through Celite and the filtrate is concentrated to dryness. The residue is chromatographed on a silica gel column (15×2.5 cm.) using the lower phase of a chloroform-methanol-concentrated ammonium hydroxide solution (2:1:1) as the eluant to give 3,6′-di-N-(2,2,2-trichloroethoxycarbonyl)kanamycin A as a colorless amorphous solid; $[\alpha]_D^{26}$ +68.0° (CH$_3$OH); $\nu$ max (nujol) 3400, 1720, 1050 cm$^{-1}$; $\delta$ (CD$_3$OD) ~4.75 ppm (4H, s, Cl$_3$CC$\underline{H_2}$OCO—).

E. 3,6′-Di-N-(4-Methoxybenzyloxycarbonyl)-Kanamycin A

Kanamycin A (30 g.) is dissolved in dimethylsulfoxide (1.2 l.) containing nickel acetate (98.1 g.) and the mixture is stirred at 25° C. for 0.5 hour. 4-Methoxybenzyl-S-(4,6-dimethylpyrimidin-2-yl)-thiolcarbonate (37.6 g.) in dimethylsulfoxide (200 ml.) is added dropwise over 40 minutes. Additional reagent (3×3.76 g.), dissolved in dimethylsulfoxide (3×10 ml.) is added in portions at 1.5 hour intervals. After a total of 5 hours, the mixture is diluted successively with diethylether (3×3 l.) and the ether layer is decanted leaving a dark green gum. The latter is dissolved in methanol (100 ml.) and hydrogen sulfide is passed through the solution for 0.5 hour. The mixture is filtered and the filtrate is concentrated to a volume of 20 ml. and then added to diethylether (1 l.) at 0° C. The ether is decanted and the residual gum is taken up in methanol (10 ml.) and added dropwise to diethylether (1 l.) at 0° C. The resulting precipitate is filtered off and dried, affording 3,6′-di-N-(4-methoxybenzyloxycarbonyl)-kanamycin A as a colorless amorphous solid: $[\alpha]_D^{26}$ +66.4° (CH$_3$OH), $\nu$ max (Nujol) 3300, 1720, 1700, 1520, 1250, 1040 cm$^{-1}$, $\delta$ (d$_6$—DMSO) 3.74 (6H, s, —C$_6$H$_4$OC$\underline{H_3}$), 4.80 (4H, s, —C$\underline{H_2}$C$_6$H$_4$OCH$_3$), 6.87 (4H, m, —C$_6$$\underline{H_4}$OCH$_3$) and 7.25 ppm (4H, m, —C$_6$$\underline{H_4}$OCH$_3$).

F. 1-N-(4-Methoxybenzyloxycarbonyl-3,6′-Di-N-(2,2,2-Trichloroethoxycarbonyl)kanamycin A 3,6′-Di-N-(2,2,2-trichloroethoxycarbonyl)kanamycin A (1.78 g.) is dissolved in dioxane-water (1:1) containing N-(4-methoxybenzyloxycarbonyloxy)phthalimide (748 mg.) and the mixture is stirred at 25° C. Additional reagent (374 mg.) is added after 3 hours and, after a total of 5 hours, Amberlite IRA-401S (OH$^\ominus$) resin is added to the mixture. After stirring for 0.5 hour, a mixture of dioxane-methanol (1:1) (100 ml.) is added and the stirring is continued for 1 hour. The mixture is filtered and the resin is washed with a 1% solution of ammonium hydroxide in dioxane-methanol (1:1) (1 l.) The combined filtrates are evaporated to dryness and the residue chromatographed on a silica gel column (60×2.5 cm.) using the lower phase of a chloroform-methanol-concentrated ammonium hydroxide-dioxane solution (2:1:10.8) as the eluant to give 1-N-(4-methoxybenzyloxycarbonyl)-3,6′-di-N-(2,2,2-trichloroethoxycarbonyl)-kanamycin A as a colorless amorphous solid; $[\alpha]_D^{26}$ +59.7° (CH$_3$OH); $\nu$ max (nujol) 3400, 1720, 1050 cm.$^{-1}$; $\delta$ (d$_6$—DMSO) 3.72 (3H, s, C$\underline{H_3}$OC$_6$H$_4$C-H$_2$OCO—), 4.78 (4H, s, Cl$_3$CC$\underline{H_2}$OCO—), 4.90 (2H, s, CH$_3$OC$_6$H$_4$C$\underline{H_2}$OCO—), 6.87 (2H, m, CH$_3$OC$_6$$\underline{H_4}$C-H$_2$OCO—) and 7.25 ppm. (2H, m, CH$_3$OC$_6$$\underline{H_4}$C-H$_2$OCO—).

G. 1-N-(4-Methoxybenzyloxycarbonyl)-3,6′,3″-tri-N-(2,2,2-Trichloroethoxycarbonyl)Kanamycin A 1-N-(4-Methoxybenzyloxycarbonyl)-3,6′-di-N-(2,2,2-trichloroethoxycarbonyl)kanamycin A (0.96 g.) is dissolved in tetrahydrofuran-water (2:1) (20 ml.) containing triethylamine (97 mg.) and N-[2-(2,2,2-trichloroethoxycarbonylamino)ethoxycarbonyloxy]succinimide (2.8 g.) is added and the mixture is stirred at 25° C. for 18 hours. The solution is concentrated and the resulting gum is chromatographed on a silica gel column (60×2.5 cm.) using the lower phase of a chloroform-methanol-concentrated ammonium hydroxide solution (2:1:1) as the eluant to give 1-N-(4-methoxybenzyloxycarbonyl)-3,6′,3″-tri-N-(2,2,2-trichloroethoxycarbonyl)kanamycin A as a colorless amorphous solid; $[\alpha]_D^{26}$ +34.2° (CH$_3$OH), $\nu$ max (nujol) 3300, 1710, 1030 cm.$^{-1}$; $\delta$ (d$_6$—DMSO) 3.71 (3H, s, —C$_6$H$_4$OC$\underline{H_3}$), 4.70–4.90 (8H, s, —C$\underline{H_2}$CCl$_3$, —C$\underline{H_2}$C$_6$H$_4$OCH$_3$), 6.84 (2H, m, —C$_6$$\underline{H_4}$OCH$_3$) and 7.22 ppm (2H, m, —C$_6$$\underline{H_4}$OCH$_3$).

H. 3,6′,3″-Tri-N-(2,2,2-Trichloroethoxycarbonyl)-Kanamycin A

1-N-(4-Methoxybenzyloxycarbonyl)-3,6′,3″-tri-N-(2,2,2-trichloroethoxycarbonyl)kanamycin A (500 mg.) is dissolved in trifluoroacetic acid (1 ml.) and allowed to remain at 25° C. for 3 minutes. The solution is evaporated under reduced pressure and the residue is azeotroped with toluene. The residue is chromatographed on a silica gel column (60×1.5 cm.) using the lower phase of a chloroform-methanol-14% ammonium hydroxide solution (2:1:1) as the eluant to give 3,6',3''-tri-N-(2,2,2-trichloroethoxycarbonyl)kanamycin A as a colorless amorphous solid; $[\alpha]_D^{26}$ +69.9° (DMSO); $\nu$ max (nujol) 3250, 1720, 1510, 1020 cm.$^{-1}$; $\delta$ (CD$_3$OD) 4.85 ppm (6H, s, —CH$_2$CCl$_3$).

I. 3,2',6'-Tri-N-(4-Methoxybenzyloxycarbonyl)-Sisomicin

Sisomicin (1 g.) is dissolved in dimethylsulphoxide (35 ml.) containing cobalt (II) acetate (2 g.). The mixture is stirred at 25° C. for 0.5 hour. 4-Methoxybenzyl-S-(4,6-dimethylpyrimidin-2-yl)-thiolcarbonate (2 g.) is added and the mixture is stirred at 25° C. for 1 hour. Additional reagent (0.2 g.) is added and after a further hour, the mixture is poured into 2 N ammonium hydroxide (500 ml.) and the mixture is stirred for 2 hours. The mixture is extracted with chloroform (3×300 ml.) and the chloroform layer is dried (MgSO$_4$) and evaporated. The resultant gum is dissolved in the minimum volume of methanol and then added dropwise to diethylether (500 ml.). The crude product is filtered off and chromatographed on a silica gel column (30×2.5 cm.) using 10% methanol in chloroform as the eluant to give 3,2',6'-tri-N-(4-methoxybenzyloxycarbonyl)sisomicin as a colorless amorphous solid; $[\alpha]_D^{26}$ +113.9° (CH$_3$OH); $\nu$ max (Nujol) 3250, 1670, 1510, 1490, 1025 cm.$^{-1}$; $\delta$ (d$_6$—DMSO) 1.00 (3H, s, 4''—CH$_3$), 3.75 (9H, s, —C$_6$H$_4$OCH$_3$), 4.93 (6H, s, —CH$_2$C$_6$H$_4$OCH$_3$), 6.88 (6H, m, —C$_6$H$_4$OCH$_3$) and 7.28 ppm (6H, m, —C$_6$H$_4$OCH$_3$).

EXAMPLES

EXAMPLE 1

1-N-Substituted-Poly and Per-N-Protected-4,6-Di-O-(Aminoglycosyl)-1,3-Diaminocyclitols A. 3,6'-Di-N-Benzyloxycarbonyl-1-N-(2-Benzyloxycarbonylaminoethoxycarbonyl)gentamicin B 3,6'-Di-N-benzyloxycarbonylgentamicin B (200 mg.) is dissolved in methanol-water (1:1) (5 ml.) and triethylamine is added until the mixture reaches pH 10. N-(2-Benzyloxycarbonylaminoethoxycarbonyloxy)succinimide (98 mg.) is added and the mixture is stirred at 25° C. for 3 hours. The solution is evaporated to dryness and the residue chromatographed on a silica gel column (120×2 cm.) using the lower phase of a chloroform-methanol-7% ammonium hydroxide solution (2:1:1) as the eluant to give 3,6'-di-N-benzyloxycarbonyl-1-N-(2-benzyloxycarbonylaminoethoxycarbonyl)gentamicin B as a colorless amorphous solid; $[\alpha]_D^{26}$ +63.4° (CH$_3$OH); $\nu$ max (KBr) 3310, 1700, 1540, 1045 cm$^{-1}$; $\delta$ (DMSO-d$_6$) 1.00 (3H, broad s, 4''—CH$_3$), 2.50 (3H, broad s, 3''—NCH$_3$), 5.00 (6H, broad s, —CH$_2$C$_6$H$_5$) and 7.30 ppm (15H, broad s, —CH$_2$C$_6$H$_5$).

B. 3,6',3''-Tri-N-Benzyloxycarbonyl-1-N-(2-Benzyloxycarbonylaminoethoxycarbonyl)gentamicin B 3,6',3''-Tri-N-benzyloxycarbonylgentamicin B (2.0 g.) is dissolved in dry dimethylformamide (100 ml.) and triethylamine (228 mg.). N-(2-Benzyloxycarbonylaminoethoxycarbonyloxy)succinimide (759 mg.) is added and the mixture stirred under dry argon at 25° C. for 3 hours. The solution is evaporated to dryness and the residue chromatographed on a silica gel column (110×2.5 cm.) using the lower phase of a chloroform-methanol-7% ammonium hydroxide solution (2:1:1) as the eluant to give 3,6',3''-tri-N-benzyloxycarbonyl-1-N-(2-benzyloxycarbonylaminoethoxycarbonyl)-gentamicin B as a colorless amorphous solid; $[\alpha]_D^{26}$ +60.7° (CH$_3$OH), $\nu$ max (KBr), 3350, 1695, 1515, 1040 cm$^{-1}$; $\delta$ (CDCl$_3$), 1.00 (3H, broad s, 4''—CH$_3$), 2.95 (3H, broad s, 3''—NCH$_3$), 5.00 (8H, broad s, —CH$_2$C$_6$H$_5$) and 7.25 ppm. (20H, broad s, —CH$_2$C$_6$H$_5$).

C. 3,6'-Di-N-Benzyloxycarbonyl-1-N-(2-Benzyloxycarbonylaminoethoxycarbonyl)kanamycin A 3,6'-Di-N-benzyloxycarbonylkanamycin A (1 g.) is dissolved in a mixture of water (10 ml.) and dioxane (5 ml.). Triethylamine is added until the pH reaches 9. N-(2-Benzyloxycarbonylaminoethoxycarbonyloxy)succinimide (427 mg.) in dioxane (10 ml.) is added dropwise over 0.5 hours. The reaction mixture is then stirred at 25° C. for 3 hours. The solution is evaporated to dryness and chromatographed on a silica gel column (110×1.5 cm.) using the lower phase of a chloroform-methanol-concentrated ammonium hydroxide solution (2:1:1) as the eluant to give 3,6'-di-N-benzyloxycarbonyl-1-N-(2-benzyloxycarbonylaminoethoxycarbonyl)kanamycin A as a colorless amorphous solid; $[\alpha]_D^{26}$+49.7° (CH$_3$OH—H$_2$O) (1:1); $\nu$ max (KBr), 3325, 1680, 1535, 1045 cm$^{-1}$; $\delta$ (DMSO—d$_6$), 5.02 (6H, broad s, —CH$_2$C$_6$H$_5$) and 7.37 ppm. (15H, broad s, —CH$_2$C$_6$H$_5$).

D. 3,6',3''-Tri-N-Benzyloxycarbonyl-1-N-(3-Benzyloxycarbonylaminopropoxycarbonyl)gentamicin B 3,6',3''-Tri-N-benzyloxycarbonylgentamincin B (1.8 g.) is dissolved in dry dimethylformamide (100 ml.) and triethylamine (210 mg.). N-(3-Benzyloxycarbonylaminopropoxycarbonyloxy)succinimide (780 mg.) is added and the mixture stirred at 25° C. for 18 hours. The solution is evaporated to dryness and the residue chromatographed on a silica gel column (110×3.5 cm.) using the lower phase of a chloroform-methanol-7% ammonium hydroxide solution (2:1:1) as the eluant to give 3,6',3''-tri-N-benzyloxycarbonyl-1-N-(3-benzyloxycarbonylaminopropoxycarbonyl)gentamicin B as a colorless amorphous solid; $[\alpha]_D^{26}$ +47.2° (CHCl$_3$); $\nu$ max (KBr) 3350, 1700, 1050 cm$^{-1}$; $\delta$ (CDCl$_3$) 1.00 (3H, broad s, 4''—CH$_3$), 2.95 (3H, broad s, 3''—CH$_3$), 5.01 (8H, broad s, —CH$_2$ C$_6$H$_5$) and 7.25 ppm. (20H, broad s, —CH$_2$C$_6$H$_5$).

E. 3,6'-Di-N-Benzyloxycarbonyl-1-N-(4-Benzyloxycarbonylaminobutoxycarbonyl)gentamicin B 3,6'-Di-N-benzyloxycarbonylgentamicin B (1.5 g.) is dissolved in methanol-water (1:1) (100 ml.) and triethylamine is added until the pH reaches 9.0. N-(4-Benzyloxycarbonylaminobutoxycarbonyloxy)succinimide (729 mg.) is added and the mixture stirred at 25° C. for 3 hours. Additional succinimide reagent (729 mg.) is added and the mixture stirred at 25° C. for 18 hours. The solution is evaporated to dryness and the residue chromatographed on a silica gel column (60×3.5 cm.) using the lower phase of a chloroform-methanol-14% ammonium hydroxide solution (2:1:1) as the eluant to give 3,6'-di-N-benzyloxycarbonyl-1-N-(4-benzyloxycarbonylaminobutoxycarbonyl)gentamicin B as a colorless amorphous solid; $[\alpha]_D^{26}$ +51.8° (CHCl$_3$); $\nu$ max (KBr) 3320, 1700, 1530, 1050 cm$^{-1}$; $\delta$ (CDCl$_3$) 1.09 (3H, broad s, 4''—CH$_3$), 1.50 (4H, broad m, CbzNHCH$_2$(CH$_2$)$_2$CH$_2$O—), 2.49 (3H, broad s, 3''—NCH$_3$), 5.01 (6H, broad s, C$_6$H$_5$CH$_2$—) and 7.15–7.28 ppm. (15H, s, C$_6$H$_5$CH$_2$—).

F. (2R)-3,6'-Di-N-Benzyloxycarbonyl-1-N-(2-Benzyloxycarbonylaminobutoxycarbonyl)gentamicin B 3,6'-Di-N-benzyloxycarbonylgentamicin B (1.5 g.) is dissolved in methanol-water (1:1) (100 ml.) and triethylamine is added until the pH reaches 9.0. (2R)-N-(2-Benzyloxycarbonylaminobutoxycarbonyloxy)succinimide (728 mg.) is added and the mixture stirred at 25° C. for 3 hours. The mixture is evaporated to dryness and the residue chromatographed on a silica gel column (60×2 cm.) using the lower phase of a chloroform-methanol-14% ammonium hydroxide solution (2:1:1) as the eluant to give (2R)-3,6'-di-N-benzyloxycarbonyl-1-N-(2-benzyloxycarbonylaminobutoxycarbonyl)gentamicin B as a colorless amorphous solid; $[\alpha]_D^{26}$ +66.1° (DMSO); $\nu$ max (KBr), 3320, 1695, 1540, 1050 cm$^{-1}$; $\delta$ (d$_6$—DMSO), 0.83 (3H, t, J 6Hz, $\underline{CH_3}$CH$_2$—), 1.19 (3H, s, 4''—CH$_3$), 5.00 (6H, s, C$_6$H$_5$$\underline{CH_2}$—), 7.29 (5H, s, C$_6$$\underline{H_5}$CH$_2$—), and 7.33 ppm. (10$\underline{H}$, s, C$_6$H$_5$CH$_2$—).

G. (2S)-3,6'-Di-N-Benzyloxycarbonyl-1-N-(2-Benzyloxycarbonylamino-4-methylpentoxycarbonyl)gentamicin B 3,6'-Di-N-benzyloxycarbonylgentamicin B (4 g.) is dissolved in methanol-water (1:1) (100 ml.) and triethylamine is added until the pH reaches 9.0. (2S)-N-(2-Benzyloxycarbonylamino-4-methylpentoxycarbonyloxy)succinimide (2.09 g.) is added and the mixture stirred at 25° C. for 3 hours. Additional (2S)-N-(2-benzyloxycarbonylamino-4-methylpentoxycarbonyloxy)succinimide (2.09 g.) is added and the mixture stirred at 25° C. for a further 18 hours. The mixture is evaporated to dryness and the residue chromatographed on a silica gel column (120×5 cm.) using the lower phase of a chloroform-methanol-14% ammonium hydroxide solution (2:1:1) as the eluant to give (2S)-3,6'-di-N-benzyloxycarbonyl-1-N-(2-benzyloxycarbonylamino-4-methylpentoxycarbonyl)gentamicin B as a colorless solid; $[\alpha]_D^{26}$ +62.0° (DMSO); $\nu$ max, (KBr), 3500, 3350, 1700, 1680, 1540, 1520, 1050 cm$^{-1}$ $\delta$ (d$_6$—DMSO) 0.84 (6H, d, J 6Hz, (CH$_3$)$_2$CH—), 1.23 (3H, s, 4''—CH$_3$), 5.01 (6H, s, C$_6$H$_5$$\underline{CH_2}$—), 7.30 (5H, s, C$_6$$\underline{H_5}$CH$_2$—) and 7.33 ppm. (10$\underline{H}$, s, C$_6$$\underline{H_5}$CH$_2$—).

H. 3,2',6'-Tri-N-(2,2,2-Trichloroethoxycarbonyl)-1-N-[2-(2,2,2-Trichloroethoxycarbonylamino)ethoxycarbonyl]gentamicin C$_{1a}$ 3,2',6'-Tri-N-(2,2,2-trichloroethoxycarbonyl)gentamicin C$_{1a}$ (2 g.) is dissolved in methanol-water (1:1) (40 ml.) containing N-[2-(2,2,2-trichloroethoxycarbonylamino)ethoxycarbonyloxy]succinimide (755 mg.) and the mixture is stirred at 25° C. for 1 hour. Additional reagent (151 mg.) is added and the stirring continued for 2 hours. The solution is evaporated to dryness and chromatographed on a silica gel column (60×2.5 cm.) using 7% methanol in chloroform as the eluant to give 3,2',6'-tri-N-(2,2,2-trichloroethoxycarbonyl)-1-N-[2-(2,2,2-trichloroethoxycarbonylamino)ethoxycarbonyl]gentamicin C$_{1a}$ as a colorless amorphous solid; $[\alpha]_D^{26}$ +58.0° (CH$_3$OH); $\nu$ max (Nujol) 3350, 2920, 1730, 1560, 1470, 1045 cm.$^{-1}$; $\delta$ (d$_6$—DMSO) 1.04 (3H, s, 4''—CH$_3$), 2.50 (3H, s, 3''—NCH$_3$), and 4.78 ppm. (8H, s, —COO$\underline{CH_2}$CCL$_3$).

I. 3,2',6'-Tri-N-(2,2,2-Trichloroethoxycarbonyl)-1-N-[2-(2,2,2-Trichloroethoxycarbonylamino)ethoxycarbonyl]sisomicin 3,2',6'-Tri-N-(2,2,2-trichloroethoxycarbonyl)sisomicin (1.7 g.) is dissolved in methanol-water (1:1) (15 ml.) containing N-[2-(2,2,2-trichloroethoxycarbonylamino)ethoxycarbonyloxy]succinimide (906 mg.) and the mixture is stirred at 25° C. for 3.5 hours. The solution is evaporated to dryness and the residue is chromatographed on a silica gel column (15×2.5 cm.) using 7% methanol in chloroform as the eluant to give 3,2',6'-tri-N-(2,2,2-trichloroethoxycarbonyl)-1-N-[2-(2,2,2-trichloroethoxycarbonylamino)ethoxycarbonyl]sisomicin; $[\alpha]_D^{26}$ +77.5° (CH$_3$OH); $\nu$ max (Nujol) 3350, 2970, 2900, 1740, 1560, 1530, 1250, 1050 cm.$^{-1}$; $\delta$ (CD$_3$OD) 1.17 (3H, s, 4''—CH$_3$), 2.53 (3H, s, 3''—NCH$_3$) and 4.75 ppm. (8H, s, —COO$\underline{CH_2}$CCl$_3$).

J. 3,2',6'-Tri-N-(2,2,2-Trichloroethoxycarbonyl)-1-N-[2-(2,2,2-Trichloroethoxycarbonylamino)-ethoxycarbonyl]-5-epi-sisomicin 3,2',6'-Tri-N-(2,2,2-trichloroethoxycarbonyl)-5-epi-sisomicin (1.58 g.) is dissolved in methanol:water (1:1) (15 ml.). N-[2-(2,2,2-Trichloroethoxycarbonylamino)ethoxycarbonyloxy]succinimide (597 mg.) is added and the mixture is stirred at 25° C. for 1 hour, whereupon additional reagent (60 mg.) is added. After a total of 2 hours, the mixture is evaporated to dryness and the residue is chromatographed on a silica gel column (60×2.5 cm.) using 7% methanol in chloroform as the eluant to give 3,2',6'-tri-N-(2,2,2-trichloroethoxycarbonyl)-1-N-[2-(2,2,2-trichloroethoxycarbonylamino)-ethoxycarbonyl]-5-epi-sisomicin: $[\alpha]_D^{26}$ +74.3° (CHCl$_3$); $\nu$ max (Nujol) 3300, 1710, 1680, 1520, 1040 cm.$^{-1}$; $\delta$ (d$_6$—DMSO) 4.78 ppm (8H, s, —$\underline{CH_2}$CCl$_3$).

3,6',3''-Tri-N-Benzyloxycarbonyl-1-N-(2-Azidoethylcarboxamido)gentamicini B

2-Chloroethylisocyanate (584 mg.) and sodium iodide (834 mg.) is dissolved in dry dimethylformamide (10 ml.) and the mixture is heated at 60° C. for 18 hours. The solution is cooled to 25° C. and sodium azide (361 mg.) is added and the mixture is stirred at 25° C. for 18 hours. The resulting crude solution of 2-azidoethylisocyanate is used without further purification.

3,6',3''-Tri-N-benzyloxycarbonylgentamicin B (500 mg.) is dissolved in dry dimethylformamide (5 ml.) and the solution of 2-azidoethylisocyanate (2 ml.) is added. The mixture is stirred at 25° C. for 3 hours under dry argon. The solution is evaporated to dryness and the residue is chromatographed on a silica gel column (120×3 cm.) using the lower phase of a chloroform-methanol-14% ammonium hydroxide solution (2:1:1) as the eluant to give 3,6',3''-tri-N-benzyloxycarbonyl-1-N-(2-Azidoethylcarboxamido)gentamicin B as a colorless amorphous solid; $[\alpha]_D^{26}$ +75.7° (CH$_3$OH); $\nu$ max (CCl$_4$) 3700, 3350, 2950, 2110, 1730, 1720, 1690, 1550, 1530, 1060 cm.$^{-1}$; $\delta$ (CDCl$_3$) 1.15 (3H, broad m, 4''—CH$_3$), 3.00 (3H, broad m, 3''—NCH$_3$), 5.00 (6H, broad m, —$\underline{CH_2}$C$_6$H$_5$) and 7.27 ppm. (15H, s, —$\underline{CH_2}$C$_6$H$_5$).

L. 3,6',3''-Tri-N-(2,2,2-Trichloroethoxycarbonyl)-1-N-(2-Azidoethylthiocarboxamido)kanamycin A In a manner similar to that in Example 1K, by substituting 2-chloroethylisothiocyanate for 2-chloroethylisocyanate there is obtained 2-azidoethylisothiocyanate.

3,6',3''-Tri-N-(2,2,2-Trichloroethoxycarbonyl)kanamycin A (2 g.) is dissolved in dry dimethylformamide (20 ml.) and the solution of 2-azidoethylisothiocyanate (8 ml.) is added. The mixture is stirred at 25° C. for 3 hours under dry argon. The solution is evaporated to dryness and the residue is chromatographed on a silica gel column (120×3 cm.) using the lower phase of a chloroform-methanol-14% ammonium hydroxide solution (2:1:1) as the eluant to give 3,6',3''-tri-N-(2,2,2-trichloroethoxycarbonyl)-1-N-(2-azidoethylthiocarboxamido)kanamycin A as a colorless amorphous solid.

M. 3,2',6'-Tri-N-(4-Methoxybenzyloxycarbonyl)-1-N-[2-(4-Methoxybenzyloxycarbonylamino)-ethoxycarbonyl]sisomicin 3,2',6'-Tri-N-(4-methoxybenzyloxycarbonyl)-sisomicin (1 g.) is dissolved in aqueous methanol (1:1) (15 ml.) containing N-[2-(4-methoxybenzyloxycarbonylamino)-ethoxycarbonyloxy]succinimide (389 mg.). The reaction mixture is stirred at 25° C. for 1 hour, whereupon additional reagent (39 mg.) is added. After stirring for a further 1 hour, the mixture is evaporated to dryness and the residue is chromatographed on a silica gel column (60×2.5 cm.) using 7% methanol in chloroform as the eluant to give 3,2',6'-tri-N-(4-methoxybenzyloxycarbonyl)-1-N-[2-(4-methoxybenzyloxycarbonylamino)-ethoxycarbonyl]sisomicin as a colorless amorphous solid; $[\alpha]_D^{26}$ +69.3° (DMSO); $\nu$ max (Nujol) 3250, 1690, 1680, 1530, 1510, 1240, 1030 cm.$^{-1}$; $\delta$ (d$_6$—DMSO) 1.00 (3H, s, 4"—CH$_3$), 3.75 (12H, s, —C$_6$H$_4$O$\underline{CH_3}$), 4.94 (8H, s, —$\underline{CH_2}$C$_6$H$_4$OCH$_3$), 6.88 (8H, m, —C$_6\underline{H_4}$OCH$_3$) and 7.26 ppm (8H, m, —C$_6\underline{H_4}$OCH$_3$).

EXAMPLE 2

1-N-Substituted-4,6-di-O-(aminoglycosyl)-1,3-diaminocyclitols

A. 1-N-(2-Aminoethoxycarbonyl)gentamicin B (1) 3,6',3"-Tri-N-benzyloxycarbonyl-1-N-(2-benzyloxycarbonylaminoethoxycarbonyl)gentamicin B (1.84 g.) is dissolved in methanol (50 ml.) and 10% palladium-on-carbon (1.28 g.) is added. The mixture is hydrogenated at 55 psi at 25° C. for 18 hours. The catalyst is filtered off, washed with methanol and the filtrate evaporated to dryness. The residue is chromatographed on a silica gel column (120×2 cm.) using the lower phase of a chloroform-methanol-concentrated ammonium hydroxide solution (1:1:1) as the eluant to give 1-N-(2-aminoethoxycarbonyl)gentamicin B as a colorless amorphous solid after passage over Amberlite IRA-401S (OH$^\ominus$) resin followed by lyophilization; $[\alpha]_D^{26}$ +130.4° (H$_2$O); $\nu$ max (KB4) 3350, 1700, 1535, 1045 cm$^{-1}$; $\delta$ (D$_2$O) 1.20 (3H, s, 4"—CH$_3$), 2.50 (3H, s, 3"—NCH$_3$), 2.88 (2H, t, J 6 Hz, —OCH$_2$$\underline{CH_2}$NH$_2$), 4.11 (2H, t, J 6 Hz, —O$\underline{CH_2}$CH$_2$NH$_2$), 5.10 (1H, d, J$_1$",$_2$" 4 Hz, H$_1$" ) and 5.33 ppm. (1H, d, J$_1$',$_2$' 3.5 Hz H$_1$').

(2) 3,6'-Di-N-benzyloxycarbonyl-1-N-(2-benzyloxycarbonylaminoethoxycarbonyl)gentamicin B (50 mg.) is dissolved in methanol (10 ml.) and 10% palladium-on-carbon (30 mg.) is added. Dry hydrogen chloride (4 eq.) in methanol is added and the mixture hydrogenated at 55 psi at 25° C. for 18 hours. The product is isolated as in (1) above to give 1-N-(2-aminoethoxycarbonyl)gentamicin B.

B. 1-N-(2-Aminoethoxycarbonyl)kanamycin A (1) 3,6'-Di-N-benzyloxycarbonyl-1-N-(2-benzyloxycarbonylaminoethoxycarbonyl)kanamycin A is dissolved in methanol-dioxane-water (2:1:1) (20 ml.) and 1 N hydrochloric acid (5.3 ml.) and 10% palladium-on-carbon (840 mg.) is added. The mixture is hydrogenated at 25° C. at 55 psi, and after 2 hours, additional catalyst (840 mg.) is added. The hydrogenation is allowed to proceed for an additional 16 hours. The catalyst is filtered off and Amberlite IRA-401S (OH$^\ominus$) resin is added to the filtrate until the pH reaches 10. The mixture is filtered, and the filtrate evaporated to dryness. The residue is chromatographed on a silica gel column (120×2.5 cm.) using the lower phase of a chloroform-methanol-concentrated ammonium hydroxide solution (1:1:1) as the eluant to give 1-N-(2-aminoethoxycarbonyl)kanamycin A as a colorless amorphous solid after passage over Amberlite IRA-401S (OH$^\ominus$) resin followed by lyophilization; $[\alpha]_D^{26}$ +87.0° (H$_2$O); $\nu$ max (KBr), 3350, 1690, 1585, 1540, 1030 cm$^{-1}$; $\delta$ (D$_2$O-DCl) (pH 3), 4.18 (2H, t, J 6 Hz, —O$\underline{CH_2}$CH$_2$NH$_2$), 5.07 (1H, d, J$_1$",$_2$" 3.5 Hz, H$_1$") and 5.39 ppm (1H, d, J$_1$',$_2$' 3 Hz, H$_1$').

(2) 3,6'-Di-N-(4-methoxybenzyloxycarbonyl)kanamycin A (4 g.) is dissolved in a mixture of dioxane (20 ml.) and water (40 ml.). Triethylamine is added until the pH reaches 9.0. N-[2-(4-Methoxybenzyloxycarbonylamino)ethoxycarbonyloxy]-succinimide (2.04 g.) is dissolved in dioxane (10 ml.) and is added dropwise over a period of 0.5 hour. After 2 hours at 25° C. the solution is evaporated to dryness. The residue is dissolved in trifluoroacetic acid (3 ml.) and after 3 minutes at 25° C., the solution is evaporated to dryness in vacuo and the residue is azeotroped with toluene. The product is chromatographed on a silica gel column (160×3 cm.) using chloroform:methanol:concentrated ammonium hydroxide solution (3:4:2) as the eluant to give 1-N-(2-aminoethoxycarbonyl)kanamycin A.

C. 1-N-(3-Aminopropoxycarbonyl)gentamicin B 3,6',3"-Tri-N-benzyloxycarbonyl-1-N-(3-benzyloxycarbonylaminopropoxycarbonyl)gentamicin B (1.47 g.) is dissolved in methanol (50 ml.) and 10% palladium-on-carbon (880 mg.) is added. The mixture is hydrogenated at 55 psi at 25° C. for 18 hours. Additional 10% palladium-on-carbon (880 mg.) is added and the hydrogenation is continued for a further 18 hours. The catalyst is filtered off, washed with methanol and the filtrate evaporated to dryness. The residue is chromatographed on a silica gel column (120×2 cm.) using the lower phase of a chloroform-methanol-concentrated ammonium hydroxide solution (2:1:1) as the eluant to give 1-N-(3-aminopropoxycarbonyl)gentamicin B as a colorless amorphous solid after passage over Amberlite IRA-401S (OH$^\ominus$) resin followed by lyophilization; $[\alpha]_D^{26}$ +125.7° (H$_2$O); $\nu$ max (KBr), 3350, 1700, 1050 cm$^{-1}$; $\delta$ (D$_2$O) 1.18 (3H, s, 4"—CH$_3$), 1.73 (2H, m, J=7.5 Hz, 2'"'—CH$_2$), 2.47 (3H, s, 3"—NCH$_3$), 4.09 (2H, t, J=7.5 Hz, 1'"—CH$_2$), 5.06 (1H, d, J$_1$",$_2$"=4 Hz, H$_1$") and 5.28 ppm. (1H, d, J$_1$',$_2$'=3.5 Hz, H$_1$').

D. 1-N-(4-Aminobutoxycarbonyl)gentamicin B 3,6'-Di-N-benzyloxycarbonyl-1-N-(4-benzyloxycarbonylaminobutoxycarbonyl)gentamicin B (1.48 g.) is dissolved in methanol-water (1:1) (50 ml.) containing 1 N hydrochloric acid (6.0 ml.) and 10% palladium-on-carbon (0.89 g.) is added. The mixture is hydrogenated at 55 psi at 25° C. for 2 hours. Additional 10% palladium-on-carbon (0.89 g.) is added and the hydrogenation is continued for a further 16 hours. The catalyst is filtered off and washed with aqueous methanol. The combined filtrates are treated with Amberlite IRA-401S (OH$^\ominus$) resin until pH 11.0 and then filtered. The filtrate is concentrated and the residue chromatographed first on a silica gel column (60×2.5 cm.) and then on a column (110×2.5 cm.) using the lower phase of a chloroform-methanol-concentrated ammonium hydroxide solution (1:1:1) as the eluant in each case to obtain 1-N-(4-aminobutoxycarbonyl)gentamicin B as a colorless amorphous solid after passage over Amberlite IRA-401S (OH$^\ominus$) resin followed by lyophilization; $[\alpha]_D^{26}$ +124.8° (H$_2$O) $\nu$ max (KBr), 3350, 1700, 1550, 1045 cm$^{-1}$; $\delta$ (D$_2$O), 1.21 (3H, s, 4"—CH$_3$), 1.60 (4H, m, —OCH$_2$($\underline{CH_2}$)$_2$CH$_2$NH$_2$), 2.50 (3H, s, 3"—NCH$_3$), 5.08 (1H, d, J$_1$",$_2$" 4 Hz, H$_1$") and 5.29 ppm. (1H, d, J$_1$',$_2$' 3.5 Hz, H$_1$').

E. (2R)-1-(N-2-Aminobutoxycarbonyl)gentamicin B (2R)-3,6'-Di-N-benzyloxycarbonyl-1-N-(2-benzyloxycarbonylaminobutoxycarbonyl)gentamicin B (1.6 g.) is dissolved in methanol-water (1:1) (50 ml.) containing 1 N hydrochloric acid (6.4 ml.) and 10% palladium-on-carbon (0.96 g.) is added. The mixture is hydrogenated at 55 psi at 25° C. for 2 hours. Additional 10% palladium-on-carbon (0.96 g.) is added and the hydrogenation continued for a further 16 hours. The catalyst is filtered off and washed with aqueous methanol. The combined filtrates are treated with Amberlite IRA-401S (OH⊖) resin until pH 11.0 and then filtered. The filtrate is concentrated and chromatographed on a silica gel column (60×2.5 cm.) using the lower phase of a chloroform-methanol-concentrated ammonium hydroxide solution (2:1:1) as the eluant to give (2R)-1-N-(2-aminobutoxycarbonyl)gentamicin B as a colorless amorphous solid after passage over Amberlite IRA-401S (OH⊖) resin followed by lyophilization; $[\alpha]_D^{26}$ +115.5° ($H_2O$); $\nu$ max (KBr) 3350, 1700, 1560, 1050 cm$^{-1}$; $\delta$ ($D_2O$), 0.96 (3H, t, J 7 Hz, $\underline{CH_3}CH_2$—), 1.24 (3H, s, 4'''—$CH_3$), 2.57 (3H, s, 3''—$NCH_3$), 5.12 (1H, d, $J_1'',2''$ 4 Hz, $H_1''$) and 5.36 ppm. (1H, d, $J_1',2'$ 3.5 Hz, $H_1'$).

F. (2S)-1-N-(2-Amino-4-Methoxypentoxycarbonyl)-gentamicin B (2S)-3,6'-Di-N-benzyloxycarbonyl-1-N-(2-benzyloxycarbonylamino-4-methylpentoxycarbonyl)gentamicin B (4.25 g.) is dissolved in methanol-water (1:1) (150 ml.) containing 1 N hydrochloric acid (4.3 ml.) and 10% palladium-on-carbon (2.7 g.) is added. The mixture is hydrogenated at 55 psi at 25° C. for 18 hours. The catalyst is filtered off and washed with aqueous methanol. The combined filtrates are evaporated to dryness and the residue is chromatographed on a silica gel column (120×3 cm.) using the lower phase of a chloroform-methanol-14% ammonium hydroxide solution (2:1:1) as the eluant to give (2S)-1-N-(2-amino-4-methylpentoxycarbonyl)gentamicin B as a colorless amorphous solid after passage over Amberlite IRA-401S (OH⊖) resin followed by lyophilization; $[\alpha]_D^{26}$ +109.5° ($H_2O$); $\nu$ max (KBr) 3350, 1705, 1540, 1050 cm$^{-1}$; $\delta$ ($D_2O$) 0.90 (3H, d, J 6 Hz, $(CH_3)_2CH$—), 0.92 (3H, d, J 6 Hz, $(CH_3)_2CH$—), 1.20 (3H, s, 4'''—$CH_3$), 5.10 (1H, d, $J_1'',2''$ 4 Hz, $H_1''$) and 5.31 ppm (1H, d, $J_1',2'$ 3.5 Hz, $H_1'$).

G. 1-N-(2-Aminoethoxycarbonyl)gentamicin $C_{1a}$ 3,2',6'-Tri-N-(2,2,2-trichloroethoxycarbonyl)1-N-[2-(2,2,2-trichloroethoxycarbonylamino)ethoxycarbonyl]gentamicin $C_{1a}$ (1.5 g.) is dissolved in 20% acetic acid-methanol (50 ml.) containing activated zinc powder (780 mg.) and the mixture is stirred at 25° C. for 18 hours. Additional zinc powder (390 mg.) is added and the stirring is continued for a further 4 hours. The reaction mixture is filtered through a bed of celite and the filtrate is evaporated to dryness. The residue is dissolved in water (20 ml.) and a 20% aqueous sodium carbonate solution (w/v) is added until the pH reaches 10.0. The solids are filtered off and the filtrate is evaporated to dryness. The residue is chromatographed on a silica gel column (60×2.5 cm.) using the lower phase of a chloroform-methanol-concentrated ammonium hydroxide solution (2:1:1) as the eluant to give 1-N-(2-aminoethoxycarbonyl)gentamicin $C_{1a}$ as a colorless amorphous solid after passage over Amberlite IRA-401S (OH⊖) resin followed by lyophilization; $[\alpha]_D^{26}$ +107.3° ($H_2O$), $\nu$ max (KBr) 3350, 3280, 1705, 1050; $\delta$ ($D_2O$) 1.25 (3H, s, 4'''—$CH_3$), 2.57 (3H, s, 3''—$NCH_3$), 4.18 (2H, t, —$COO\underline{CH_2}NH_2$), 5.14 (1H, d, $J_1'',2''$ 4 Hz, $H_1''$) and 5.29 ppm. (1H, d, $J_1'2'$ 4 Hz, $H_1'$).

H. 1-N-(2-Aminoethoxycarbonyl)sisomicin (1) 3,2',6'-Tri-N-(2,2,2-trichloroethoxycarbonyl)-1-N-[2-(2,2,2-trichloroethoxycarbonylamino)ethoxycarbonyl]sisomicin (1.77 g.) is dissolved in 90% aqueous acetic acid (50 ml.) containing activated zinc powder (1.86 g.) and the mixture is stirred at 25° C. for 18 hours. The reaction mixture is filtered through a bed of celite and the filtrate is evaporated to dryness. The residue is dissolved in water (10 ml.) and a 10% aqueous sodium carbonate solution (w/v) is added until the pH reaches 10.0. The solids are filtered off and the filtrate is evaporated to dryness. Treat the residue in a manner similar to Example 2G to obtain 1-N-(2-aminoethoxycarbonyl)-sisomicin as a colorless amorphous solid after passage over Amberlite IRA-401S (OH⊖) resin and lyophilization; $[\alpha]_D^{26}$+138.8°; ($H_2O$), $\nu$ max (KBr) 3350, 3275, 1705, 1680, 1045 cm.$^{-1}$; $\delta$ ($D_2O$) 1.22 (3H, s, 4'''—$CH_3$), 2.50 (3H, s, 3''—$NCH_3$), 2.57 (1H, d, $J_2'',3''$=11 Hz, $H_3''$), 2.85 (1H, t, J=6 Hz, —$COOCH_2\underline{CH_2}NH_2$), 3.70 (1H, dd, $J_1'',2''$=4 Hz, $J_2'',3''$=11 Hz, $H_2''$), 4.10 (2H, t, J=6 Hz, —$COO\underline{CH_2}CH_2NH_2$), 4.13 (1H, d, $J_5''e,5''a$=12 Hz, $H_5''e$), 4.90 (1H, m, $H_4'$), 5.11 (1H, d, $J_1'',2''$=4 Hz, $H_1''$) and 5.33 ppm. (1H, d, $J_1',2'$=3.5 Hz, $H_1'$).

(2) 3,2',6'-Tri-N-(4-methoxybenzyloxycarbonyl)-1-N-[2-(4-methoxybenzyloxycarbonylamino)ethoxycarbonyl]sisomicin (500 mg.) is added to trifluoroacetic acid (2 ml.) at 0° C. and the mixture is stirred for 5 minutes. The solution is added dropwise to diethyl ether (150 ml.) and the resulting precipitate is filtered off and chromatographed on a silica gel column (160×2.5 cm.) using the lower phase of a chloroform-methanol-14% ammonium hydroxide solution (2:1:1) as the eluant to give 1-N-(2-aminoethoxycarbonyl)sisomicin as a colorless amorphous solid after passage over Amberlite IRA-401S (OH⊖) resin followed by lyophilization. The product is identical with that prepared in (1) above.

I. 1-N-(2-Aminoethylcarboxamido)gentamicin B

In a manner similar to that in Example 2D, hydrogenate 3,6',3''-tri-N-benzyloxycarbonyl-1-N-(2-azidoethylcarboxamido)gentamicin B to obtain 1-N-(2-aminoethylcarboxamido)gentamicin B as a colorless amorphous solid after passage over Amberlite IRA-401S (OH⊖) resin followed by lyophilization; $[\alpha]_D^{26}$+99.4° ($H_2O$); $\nu$ max (KBr) 3330, 2920, 1655, 1565, 1050 cm$^{-1}$; $\delta$ ($D_2O$) 1.23 (3H, s, 4'''—$CH_3$), 2.51 (3H, s, 3''—$NCH_3$), 4.09 (1H, d, $J_5''e,5''a$ 12 Hz, $H_5''e$), 5.13 (1H, d, $J_1'',2''$ 4 Hz, $H_1''$) and 5.32 ppm (1H, d, $J_1',2'$ 3.5 Hz, $H_1'$).

J. 1-N-(2-Aminoethylthiocarboxamido)Kanamycin A 3,6',3''-Tri-N-(2,2,2-trichloroethoxycarbonyl)1-N-(2-azidoethylthiocarboxamido)kanamycin A (500 mg.) is dissolved in dioxane-methanol (1:1) (50 ml.) and Lindlar's catalyst (200 mg.) is added. The mixture is hydrogenated at 25° C. at atmospheric pressure for 18 hours. The catalyst is filtered off and the filtrate and washings combined and evaporated. The residue is dissolved in 20% acetic acid-methanol (20 ml.) and activated zinc powder (290 mg.) is added. The mixture was stirred at 25° C. 18 hours. The mixture is filtered through a bed of Celite, and the filtrate is evaporated to dryness. The residue is dissolved in water (20 ml.) and a 10% aqueous sodium carbonate solution (w/v) is added until the pH reaches 10.0. The solids are filtered off and the filtrate evaporated to dryness. The residue is chromatographed on a silica gel column (60×2.5 cm.) using the lower phase of a chloroform-methanol-concentrated ammonium hydroxide solution (1:1:1) as the eluant to give 1-N-(2-aminoethylthiocarboxamido)kanamycin A as a colorless amorphous solid after passage over Amberlite IRA-401S (OH⊖) resin followed by lyophilization.

K. 1-N-(2-Aminoethoxycarbonyl)-5-Epi-Sisomicin

In a manner similar to that in Example 2G, hydrogenate 3,2',6'-tri-N-(2,2,2-trichloroethoxycarbonyl)-1-N-[2-(2,2,2-trichloroethoxycarbonylamino)ethoxycarbonyl]-5-epi-sisomicin. The reaction mixture is then filtered through Celite and the filtrate and washings are concentrated and then dissolved in methanol (10 ml.). Concentrated ammonium hydroxide is added until the pH reaches 7.0. The mixture is evaporated to dryness and the residue is taken up in water (2 ml.) and chromatographed on an Amberlite CG-50 (NH$_2$) resin column (30×3.5 cm.). The column is initially eluted with water (1 liter) and the aqueous eluant is saved. Elution with 0.1 N, 0.15 N, 0.2 N, 0.25 N, 0.3 N, 0.35 N ammonium hydroxide (500 ml. each) gives the product in the latter fraction. The initial aqueous eluant is evaporated to dryness and the residue is dissolved in water (5 ml.). A 5% aqueous sodium bicarbonate solution is added until the pH reaches 7.0 and the mixture is filtered. The filtrate is evaporated to dryness and the solids are stirred with ethanol-free chloroform and refiltered. The filtrate is evaporated to dryness and the residue is chromatographed on a silica gel column (120×2.5 cm.) using the lower phase of a chloroform:methanol:concentrated ammonium hydroxide solution (2:1:1) as the eluant. The combined fractions of 1-N-(2-aminoethoxycarbonyl)-5-epi-sisomicin are obtained as a colorless amorphous solid after passage over Amberlite IRA-401S (OH$^\ominus$) resin followed by lyophilization; $[\alpha]_D^{26}$ +148.5° (H$_2$O) $\nu$ max (KBr) 3350, 1700, 1680, 1040 cm.$^{-1}$ $\delta$ (D$_2$O) 1.21 (3H, s, 4''—CH$_3$), 2.49 (3H, s, 3''—NCH$_3$), 2.59 (1H, d, J$_2$''a,$_3$''a=11 Hz, H$_3$''a), 2.84 (2H, t, J=6 Hz, —OCH$_2$CH$_2$NH$_2$), 4.08 (2H, t, J=6 Hz, —OCH$_2$CH$_2$NH$_2$), 4.31 (1H, m, H$_5$e), 4.87 (1H, m, H$_4$'), 5.01 (1H, d, J$_1$''e,$_2$''a=4 Hz, H$_1$''e) and 5.10 ppm (1H, d, J$_1$'e,$_2$'a=2 Hz, H$_1$'e).

L. Other 1-N-Substituted-4,6-Di-O-(Aminoglycosyl)-1,3-Diaminocyclitols (1) In a manner similar to that described in Example 2B(2), the 1,3''-N-unprotected-per-N-(PMZ)-protected-4,6-di-O-(aminoglycosyl)-1,3-diaminocyclitols of our invention may be reacted with N-[2-(PMZ-amino)ethoxycarbonyloxy]-succinimide, N-[3-(PMZ-amino)propoxycarbonyloxy]-succinimide, N-[4-(PMZ-amino)-butoxycarbonyloxy]-succinimide to obtain, respectively, the 1-N-(2-aminoethoxycarbonyl), 1-N-(3-aminopropoxycarbonyl) and 1-N-(4-aminobutoxycarbonyl) derivatives of gentamicin A, gentamicin B, gentamicin B$_1$, gentamicin C$_1$, gentamicin C$_{1a}$, gentamicin C$_2$, gentamicin C$_{2a}$, gentamicin C$_{2b}$, gentamicin X$_2$, kanamycin A, kanamycin B, 3',4'-dideoxykanamycin B, sisomicin, verdamicin, tobramycin, Antibiotic G-52, Antibiotic G-418, Antibiotic 66-40B, Antibiotic 66-40D, Antibiotic JI-20A, Antibiotic JI-20B, the 5-epi-, 5-deoxy-, 5-epi-amino-5-deoxy- analogs of the foregoing;

and Antibiotic Mu-1, Antibiotic Mu-4, and Antibiotic Mu-5.

(2) In a manner similar to that described in Example 1L, the 1-N-unprotected-per-N-(TCEC)-protected-4,6-di-O-(aminoglycosyl)-1,3-diaminocyclitols of our invention may be reacted with 2-azidoethylisothiocyanate or 2-azidoethylisocyanate and further treated as in Example 2J to obtain, respectively, the 1-N-(2-aminoethylthiocarboxamido), and 1-N-(2-aminoethylcarboxamido) derivatives of gentamicin A, gentamicin B, gentamicin B$_1$, gentamicin C$_1$, gentamicin C$_{1a}$, gentamicin C$_2$, gentamicin C$_{2a}$, gentamicin C$_{2b}$, gentamicin X$_2$, kanamycin A, kanamycin B, 3',4'-dideoxykanamycin B, sisomicin, verdamicin, tobramycin, Antibiotic G-52, Antibiotic G-418, Antibiotic 66-40B, Antibiotic 66-40D, Antibiotic JI-20A, Antibiotic JI-20B, the 5-epi-, 5-deoxy-, 5-epi-amino-5-deoxy- analogs of the foregoing;

and Antibiotic Mu-1, Antibiotic Mu-4, and Antibiotic Mu-5.

EXAMPLE 3

Acid Addition Salts

A. Sulfate Salts (Sulfuric Acid Addition Salts)

Dissolve 5 gm. of 1-N-(2-aminoethoxycarbonyl)gentamicin B in 25 ml. of water and adjust the pH of the solution to 4.5 with 1 N sulfuric acid. Pour into about 300 ml. of methanol with vigorous agitation, continue the agitation for about 10–20 minutes and filter. Wash the precipitate with methanol and dry at about 60° C. in vacuo to obtain the corresponding 1-N-(2-aminoethoxycarbonyl)gentamicin B sulfate.

B. Hydrochloride Salts

Dissolve 5 gm. of 1-N-(2-aminoethoxycarbonyl)gentamicin B in 25 ml. of water. Acidify with 2 N hydrochloric acid to pH 5. Lyophilize to obtain the corresponding 1-N-(2-aminoethoxycarbonyl)gentamicin B hydrochloride.

FORMULATIONS

| | Formulation 1 | |
|---|---|---|
| Injectable Solution | Per 2.0 ml. Vial | Per 50 Liters |
| 1-N-(2-aminoethoxycarbonyl)-gentamicin B | 84* mgs. | 2100* gms. |
| Methylparaben, USP | 2.6 mgs. | 65.0 gms. |
| Propylparaben, USP | 0.4 mgs. | 10.0 gms. |
| Sodium bisulfite, USP | 4.8 mgs. | 120.0 gms. |
| Sodium sulfite, USP | 1.6 mgs. | 40.0 gms. |
| Disodium Ethylenediamine tetraacetate dihydrate, R.G. | 0.2 mgs. | 5.0 gms. |
| Water, USP q.s. | 2.0 ml. | 50.0 liters |

*Includes a 5% manufacturing overchange

Procedure: For a 50.0 liter batch

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25°-30° C. by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the 1-N-(2-aminoethoxycarbonyl)gentamicin B sulfate. Bring the batch volume up to 50.0 liters with water for injection and agitate until homogeneous.

Under sterile conditions, filter the solution through a suitable bacteria retentive filter collecting the filtrate in a filling tank.

Fill the filtrate aseptically into sterile pyrogenfree multiple dose vials, stopper and seal.

| Tablet | Formulation 2 | | |
|---|---|---|---|
| | 10 mg. Tab. | 25 mg. Tab. | 100 mg. Tab. |
| 1-N-(2-aminoethoxy-carbonyl)gentamicin B | 10.50* mg. | 26.25* mg. | 105.00* mg. |
| Lactose, impalpable powder | 197.50 mg. | 171.25 mg. | 126.00 mg. |
| Corn Starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |
| | 243.00 mg. | 232.50 mg. | 277.00 mg. |

*5% excess

Procedure

Prepare a slurry consisting of the 1-N-(2-aminoethoxycarbonyl)gentamicin B, lactose and polyvinylpyrrolidone. Spray dry the slurry. Add corn starch and magnesium stearate. Mix and compress into tablets on a suitable press to the specified weight.

| Formulation 3 | |
|---|---|
| Ointment | |
| 1-N-(2-aminoethoxycarbonyl)-gentamicin B | 1.0 gm. |
| Methyl paraben USP | 0.5 gm. |
| Propyl paraben USP | 0.1 gm. |
| Petrolatum | to 1000 gm. |

Procedure (1) Melt the petrolatum.

(2) Mix the 1-N-(2-aminoethoxycarbonyl)gentamicin B, methyl paraben and propyl paraben with about 10% of molten petrolatum and make a slurry. Mill the slurry and add to the balance of the petrolatum. Cool to room temperature with agitation.

We claim:

1. A 1-N-X derivative of a 4,6-di-O-(aminoglycosyl)-1,3-diaminocyclitol, wherein X is

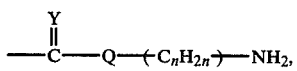

wherein

Y is O, S;
Q is O, NH;
n is 2–6;
with the provisos that:
(a) when Y is S, Q must be NH;
(b) Q and the NH$_2$ functional group cannot be attached to the same carbon atom;
and the pharmaceutically acceptable acid addition salts thereof.

2. A compound of claim 1 wherein said 4,6-di-O-(aminoglycosyl)-1,3-diaminocyclitol is selected from the group consisting of gentamicin A, gentamicin B, gentamicin B$_1$, gentamicin C$_1$, gentamicin C$_{1a}$, gentamicin C$_2$, gentamicin C$_{2a}$, gentamicin C$_{2b}$, gentamicin X$_2$, kanamycin A, kanamycin B, 3',4'-dideoxykanamycin B, sisomicin, verdamicin, tobramycin, Antibiotic G-52, Antibiotic G-418, Antibiotic 66-40B, Antibiotic 66-40D, Antibiotic JI-20A, Antibiotic JI-20B, the 5-epi-, 5-deoxy-, 5-epi-amino-5-deoxy- analogs of the foregoing;

and Antibiotic Mu-1, Antibiotic Mu-4, and Antibiotic Mu-5.

3. A compound of claim 1 wherein Y is O, Q is O, n is 2–3, and the NH$_2$ functional group is on a terminal carbon atom.

4. A compound of claim 3 which is 1-N-(2-aminoethoxycarbonyl)gentamicin B.

5. A compound of claim 3 which is 1-N-(2-aminoethoxycarbonyl)sisomicin.

6. A compound of claim 3 which is 1-N-(2-aminoethoxycarbonyl)kanamycin A.

7. A compound of claim 3 which is 1-N-(2-aminoethoxycarbonyl)gentamicin C$_{1a}$.

8. A compound of claim 3 which is 1-N-(2-aminoethoxycarbonyl)-5-epi-sisomicin.

9. A compound of claim 3 which is 1-N-(2-aminopropoxycarbonyl)gentamicin B.

10. A compound of claim 3 which is 1-N-(2-aminopropoxycarbonyl)kanamycin A.

11. A compound of claim 3 which is 1-N-(2-aminopropoxycarbonyl)sisomicin.

12. A compound of claim 3 which is 1-N-(2-aminopropoxycarbonyl)gentamicin C$_{1a}$.

13. A compound of claim 3 which is 1-N-(2-aminopropoxycarbonyl)-5-epi-sisomicin.

14. A compound of claim 3 which is 1-N-(2-aminoethylcarboxamido)gentamicin B.

15. A compound of claim 3 which is 1-N-(2-aminoethylcarboxamido)sisomicin.

16. The method of eliciting an antibacterial response in a warm-blooded animal having a susceptible bacterial infection which comprises administering to said animal a non-toxic, antibacterially effective amount of a compound of claim 1.

17. A pharmaceutical composition comprising a non-toxic, antibacterially effective amount of a compound of claim 1 together with a non-toxic, pharmaceutically acceptable carrier.

* * * * *